United States Patent [19]

Weaver

[11] 4,170,520
[45] Oct. 9, 1979

[54] APPARATUS FOR MEASURING REACTANT CONCENTRATIONS AND QUANTITIES

[75] Inventor: James C. Weaver, Wayland, Mass.

[73] Assignee: Massachusetts Institute of Technology, Cambridge, Mass.

[21] Appl. No.: 833,921

[22] Filed: Sep. 16, 1977

[51] Int. Cl.$^2$ ............................................. C12K 1/10
[52] U.S. Cl. ................................... 435/288; 435/291
[58] Field of Search ....................................... 195/127

[56] References Cited

U.S. PATENT DOCUMENTS

| | | | |
|---|---|---|---|
| 3,065,148 | 11/1962 | Ferrari, Jr. | 195/127 X |
| 3,542,649 | 11/1970 | Searcy | 195/127 X |
| 3,700,562 | 10/1972 | Morgenstern et al. | 195/127 X |
| 3,948,731 | 4/1976 | Weaver | 195/103.5 R |

Primary Examiner—Raymond N. Jones
Assistant Examiner—Robert J. Warden
Attorney, Agent, or Firm—Arthur A. Smith, Jr.; Paul J. Cook

[57] ABSTRACT

A method and apparatus is provided for determining the concentration or quantity of enzyme molecules, microorganisms or substrate molecules by monitoring directly the concentration and/or the quantity of vaporous by-product produced from the selective reaction of the molecule catalyzed with a known amount of substrate or of an enzyme or a microorganism. The apparatus comprises a membrane permeable to the vaporous product or substrate, a known amount of microorganism or an enzyme adjacent to the membrane, means for introducing a liquid sample into contact with the microorganism or enzyme within a small volume adjacent the membrane and means for measuring the amount of vaporous by-product passing through the membrane. A mass spectrometer located adjacent the membrane surface is suitable for measuring the amount of vaporous product or substrate passing through the membrane. The process is conducted by first calibrating the apparatus with a known concentration of substrate or of enzyme, and thereafter contacting a sample containing an unknown concentration of enzyme or microorganism with the substrates, or substrate with the enzyme or microorganism.

7 Claims, 1 Drawing Figure

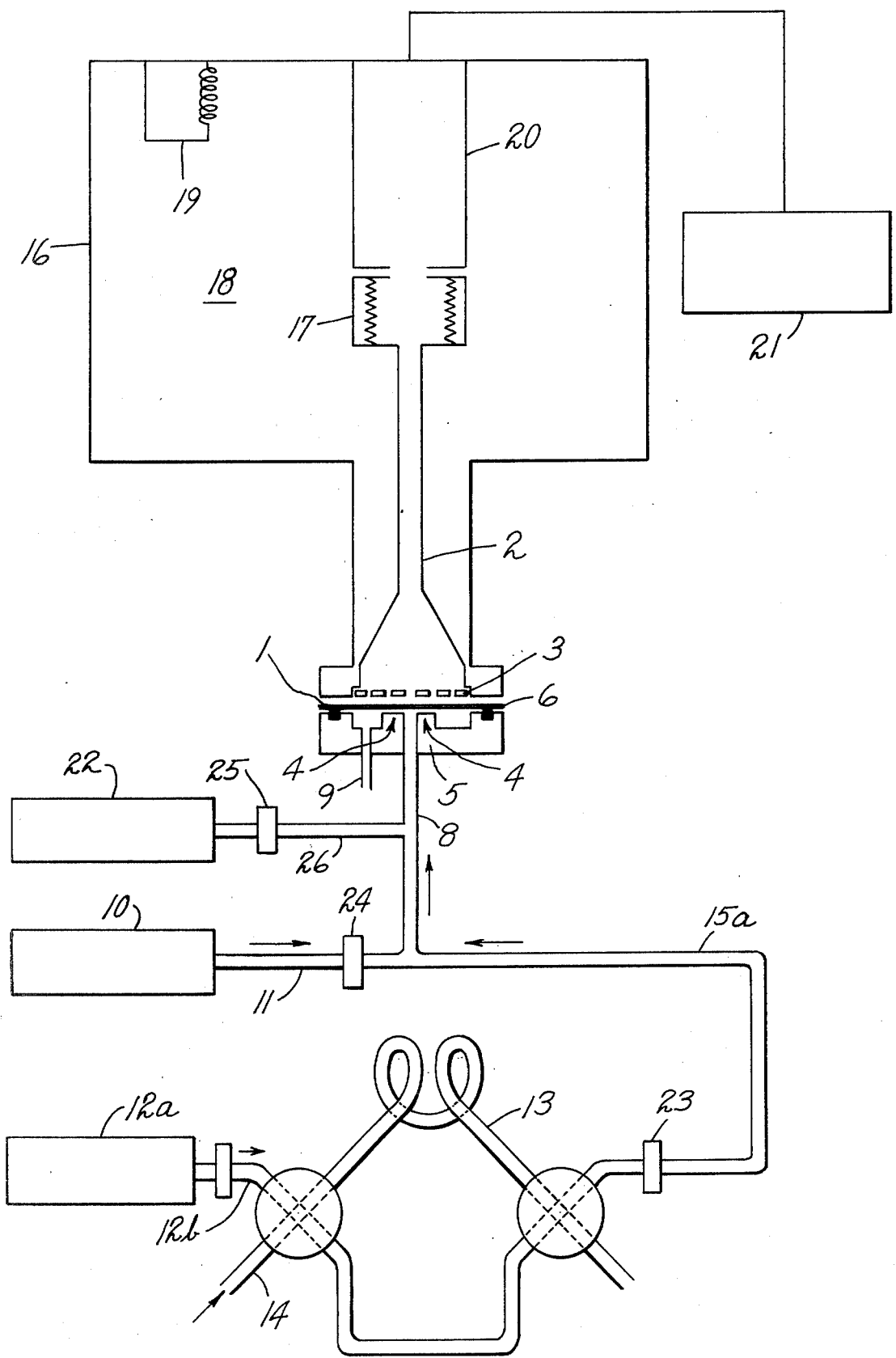

APPARATUS FOR MEASURING REACTANT CONCENTRATIONS AND QUANTITIES

BACKGROUND OF THE INVENTION

The Government has rights in this invention pursuant to Grant Nos. 1 RO1 GM22633-01 and 5 SO5 RR07047-10 awarded by the National Institute of Health.

This invention relates to a method and apparatus for measuring the concentration of a substrate, the reaction of which is catalyzed by a microorganism or an enzyme to form a vaporous product or for measuring the concentration of a microorganism or an enzyme which catalyzes the reaction of a substrate to form a vaporous product or for measuring the concentration of an inhibitor of a reaction catalyzed by a microorganism or enzyme.

Enzymes and certain microorganisms such as bacteria or yeasts are known to be selective in catalyzing a reaction involving a specific substrate. Based upon this property, these materials have been employed in a wide variety of detection techniques to determine the presence of and the concentration of the substrate. For example, enzymes and microorganisms have been employed in colormetric reactions wherein the reaction product has a different color than the starting material and the degree of color change is measured by light absorbence. This measurement then can be related to the concentration of the reactant based upon a prior-obtained calibration curve. In addition, biochemical sensors have been employed for determining the concentration of the molecules involving the use of a reference electrode and a biochemical electrode whereby change in potential is measured and this change is correlated to the concentration of the molecule. The biochemical electrode is intimately contacted with an enzyme or bacteria which enzyme or bacteria reacts selectively with the molecule being surveyed to cause a change in the potential between the biochemical electrode and the reference electrode. The use of these biochemical sensors is limited since they require the use of electrodes adapted to measure the presence of a specific ion generated during reaction are subject to interference from the same ions already present in a sample structure. Furthermore, they must be used in conjunction with an elctrolyte, which electrolyte will differ depending upon the type of electrode and type of reaction being employed. Thus, these biochemicals sensing systems are undesirably limited in that only an undesirably limited number of reactants can be monitored therewith. Furthermore, because of their bulk and because of the need for employing an electrolyte, a relatively large volume of reactant is necessary in order to obtain accurate results.

Another common method for measuring the concentration or quantity of various compounds is by means of mass spectroscopy wherein the sample to be analyzed is vaporized, ionized and subjected to an electrical or magnetic field to separate the ions on the basis of mass. While this method has wide application and is considered to be a sensitive and accurate technique, it has limitations particularly as applied to the measurement of relatively high mass molecules. This is because there is necessarily some degradation and fragmentation of relatively high mass materials during ionization resulting in a reduced detection of the material present. Also, a significant limitation in the measurement of large mass molecules is due to the complexity of their mass spectra that arises from fragmentation. Thus, direct mass spectroscopy of a mixture of large mass molecules usually yields an unuseable superposition of complicated mass spectra, so that identification and measurement of the large mass molecules in mixtures is difficult and often impossible. For this reason, it is usual to precede mass spectroscopy of mixtures by one or more separation techniques, particularly gas chromatography. Even then, however, due to overlapping gas chromatography peaks and fragmentation problems, identification and measurement can be ambiguous.

Furthermore, attempts to increase resolution of a mass spectrometer to improve selectivity in measurements results in an undesirable reduced transmission of the material being measured.

A method and apparatus for determining the concentration or quantity of molecules is disclosed in U.S. Pat. No. 3,948,731. In the apparatus, a known amount of a microorganism or enzyme is immobilized adjacent a vapor-permeable membrane. A liquid sample containing the molecules to be monitored is contacted and reacted with the immobilized enzyme. The vaporous product or substrate of the reaction is passed through the membrane and is measured by a mass spectrometer. While this procedure provides substantial advantages, particularly with regard to sensitivity, it is often undesirable in that immobilized enzymes or microorganisms are required, which, in turn, requires great care in preparation and is expensive.

It would be highly desirable to provide biochemical sensing apparatus which could be used to detect the concentrations of a wide variety of molecules. Furthermore, it would be highly desirable to provide a biochemical sensing apparatus which does not require the presence of an electrolyte and for which small volumes of samples such as physiological fluids can be tested to determine the concentration of molecules.

Furthermore, it would be highly desirable to provide a chemical sensing apparatus and a method for its use to be used to measure, in a selective manner and with extreme sensitivity, the concentration of relatively high molecular weight molecules. In addition, it would be desirable to provide such apparatus and method that eliminates the care and expense encountered in immobilizing enzymes and/or microorganisms.

SUMMARY OF THE INVENTION

This invention provides a method and apparatus for determining the concentration or quantity of molecules by monitoring directly the concentration and/or quantity of vaporous product produced from or vaporous substrate consumed by the selective reaction of the molecule catalyzed with a known amount of an enzyme or a microorganism, or if a known amount of substrate is provided, the concentration or amount of enzyme or microorganism can be determined. The apparatus comprises a membrane permeable to the vaporous product, means for injecting a known amount of a microorganism or an enzyme into a liquid containing a substrate, means for passing the liquid substrate mixed with the microorganism or enzyme into a narrow channel having a small volume adjacent the membrane and means for measuring the amount of vaporous by-product passing through the membrane. The height of the narrow channel is less than about $10^{-1}$ cm, preferably about $10^{-2}$ cm in order to maximize vapor transmission through the membrane and is less than about 10 cm in length, preferably about 1 cm in order to minimize time response and water transmission through the membrane. A mass spectrometer located adjacent the membrane surface is suitable for directly measuring the amount of vaporous by-product passing through the membrane.

BRIEF DESCRIPTION OF THE DRAWING

FIG. 1 is an elevation view of an apparatus suitable for practicing this invention.

DESCRIPTION OF SPECIFIC EMBODIMENTS

Referring to the figure, a membrane 1 such as a polysiloxane and which is permeable to vapors such as carbon dioxide is sealed adjacent guide tube 2 and is supported by perforated plate and Nuclepore filter 3. A narrow channel 4 is formed in flange 5. Channel 4 is a circular channel and is less than about 200 micrometers in height and radius of about 0.6 cm. If the dimensions of channel 4 are large, large samples are necessarily required, and frequently the sensitivity and accuracy of the concentration measurement is substantially reduced since only a small fraction of the vapors are transferred to the detector unless very long times are used. Membrane 1 is sealed to flange 5 by means of "0" ring 6. Channel 4 is provided with a liquid inlet 8 and a liquid outlet 9. A solution of a buffer and a known concentration of substrate is pumped from a pump and reservoir 10 through tube 11 to inlet 8. Pump and reservoir 12a is used to pump a buffer through a sample injection valve 13. A known volume of enzyme solution having an unknown concentration of enzymes is injected into the sample loop of the sample injection valve 13 by syringe 14. When the sample injection valve 13 is switched into the sample position, the enzyme sample is pumped by pump and reservoir 12a through tube 15a into liquid inlet 8. Further, it is often advantageous to insert continuous degassers 23 and 24 at or before the junction of tubes 11 and 15a to remove pre-existing, contaminant vapors, even though a small fraction of the enzymatically (cellularly) produced vapor may also be removed. Finally, it is also advantageous in some cases to increase the volatility of the vaporous product in the solution containing the vaporous product as it enters the narrow channel 4, which is accomplished by use of a pump and reservoir 22 which contains suitable acid or base solution. Said suitable acid or base solution can be passed through degasser 25 and tube 26 where said solution joins tube 8 in a "T".

The apparatus for measuring the vaporous by-product of the enzyme-catalyzed reaction includes a mass spectrometer, generally indicated by 16 and a vapor guide tube 2. The mass spectrometer 16 includes an ionizer 17, a vacuum chamber 18, means for forming a vacuum (not shown), a vacuum gauge 19, a mass filter 20 and recording means 21 for recording at desired mass peaks.

The operation of the apparatus of this invention will be described with reference to the use of urease and an aqueous liquid containing urea. The urease catalyzes the degradation of urea to ammonia and carbon dioxide. In the process of this invention, it is preferred to monitor the carbon dioxide at mass peak 44 rather than the ammonia product at mass peak 17 from urea in aqueous solution to obtain accurate results since the OH fragment of water, which permeates the membrane in fairly large quantity, also has mass 17. The urease sample is injected into sample loop of the sample injection valve 13. When desired, the valve is switched so that the sample is pumped with pump 12a through degasser 23 to tube 8. Concomitantly, the buffer-urea solution is pumped by pump-reservoir 10 through degasser 24 to tube 8 and mixed with the buffer-urea solution. The resultant mixture is directed into channel 4. It is desirable, but not necessary, that sufficient urea concentration (0.2 M) is used in pump-reservoir 10, so that the urease is almost saturated and maximal $CO_2$ production rate is achieved because of the small height (about 100 micrometers) of channel 4.

However, most of the carbon dioxide and some ammonia permeate the polysiloxane, which permits measurements of urease activity concentration as low as about $2 \times 10^{-4}$ international units per milliliter. During the enzymatic degradation of the urea, the carbon dioxide and ammonia permeate the polysiloxane membrane 1 and enter guide tube 2 through the perforations in the Nuclepore filter and plate 3 and pass into the ionizer 17 through guide tube 2. The gas molecules are ionized, mass selected by a quadrupole mass filter and counted in any manner well known in the art of mass spectroscopy. The residence time of the urea-urease mixture in channel 4 generally is between about 1 to 5 seconds in order to permit permeation of substantially all the carbon dioxide produced through the membrane 1 while minimizing water permeation through the membrane and providing good time response.

This invention provides substantial advantages over the prior art processes and apparatus for measuring the concentration or quantity of molecules. The apparatus of this invention is adapted to include means for measuring the presence of virtually any volatile molecule which can be passed through a membrane and therefore the apparatus is not limited for use with only a specific substrate or class of substrates. Also, the apparatus of this invention is capable of measuring indirectly the concentration of a wide variety of compounds extremely sensitively and accurately. Furthermore, the apparatus of this invention does not require the use of fluids having a specific chemical composition to perform its function. Thus, all that is required is that the physical and chemical composition of the surrounding fluid permits the enzyme or microorganism to catalyze the reaction with the reactant being tested. Furthermore, since the apparatus of this invention does not require that the reaction catalyzed by the enzyme or microorganism form a particular ion or class of ions, the particular type of enzyme or microorganism employed is not limited. Thus, any enzyme or microorganism capable of catalyzing or entering into a reaction with the substrate to form a vaporous by-product can be employed in this invention.

Also, the enzyme or microorganism need not be immobilized so that the expense and complexity of the process is substantially reduced. Furthermore, the enzymes can be utilized for a wide variety of reactions without changing the membrane.

Any available enzyme involving a volatile product or substrate, whether naturally occurring or synthetically produced and whether or not in a pure form, can be employed in the present invention. Representative suitable specific enzymes are DOPA decarboxylase, alcohol dehydrogenase, glucose oxidase, catalase, urease, pyruvate decarboxylase, lysine decarboxylase, acetylcholinesterase, histidine decarboxylase, uricase, polyphenol oxidase, acetate kinase, oxalate decarboxylase or the like. Representative suitable microorganisms are yeasts, fungi, the anaerobic bacteria and aerobic bacteria which can be employed whether separately or with enzymes to measure substrates in liquid, gasses or liquids saturated with gas. Representative suitable microorganisms include *Escherichia coli, Bacillus substillis, Clostridium sporogenes, Klebsiella aerogenes, Pseucomonas* species, *Candida* species, *Saccharomyces* species, *Fungal* spores such as from *Asperigillis niger, Actinomyces* species.

In one aspect of the present invention, more than one microorganism or enzyme can be employed. This embodiment has the advantage that it can be employed to determine the concentration of two different types of molecules in the same or in different fluids.

Furthermore, more than one enzyme or microorganism can be employed sequentially. For example, with two enzymes, one enzyme catalyzes a first reaction with the evolution of a first reaction product and this product enters into a second reaction catalyzed by a second enzyme to form a vaporous by-product. For example, lactate dehydrogenase pyruvate decarboxylase can be included to first catalyze the reaction of lactate to pyruvate. Thereafter, the pyruvate decarboxylase converts pyruvate to vaporous carbon dioxide.

Also, two or more enzymes catalyzing reactions yielding different vaporous products can be employed. For example, urease and alcohol dehydrogenase can be included with the membrane to measure urea and NADH respectively, since urease catalyzes the reaction of urea to form $CO_2$ and alcohol dehydrogenase catalyzes acetaldehyde and NADH to form ethanol and NAD. In addition, the concentration of a substrate can be measured when it is reacted with a second specific vaporous substrate in the presence of a specific enzyme or microorganism wherein the reduction of the vapor as a result of the reaction is measured directly. This procedure is applicable either to a one-step or multi-step reaction system.

In the configuration shown in the figure, the invention exhibits response behavior associated with a thin, aqueous filled channel near the bottom surface of the membrane 1. When, for example, enzyme sample to be measured is switched by valve 13 into tube 15a, there is a brief time delay while the sample is: (1) delivered to the channel 8, where mixing with substrate from tube 11 occurs, and is (2) then delivered to channel 4 and membrane 1 which is followed by an initial transient and then a steady state in which the mass spectrometer count rate is nearly constant in time. A response curve to enzyme concentration is obtained by injecting a series of different enzyme sample concentrations and recording the corresponding steady state count rate, and the count rate is proportional to the amount of vaporous product or substrate passing through channel 4. If the sample volume is sufficiently small with respect to the volume of tubes 15a and 8 and channel 4, a steady state count rate response may not be achieved, in which case the peak count rate may be used to obtain a response curve.

While this invention has been described above with reference to the use of a known amount of a substrate to determine the concentration of an enzyme or microorganism, the concentration or quantity of enzyme inhibitors, substrates or cofactors can equally well be measured. Further, this invention can also be used to measure a first substrate or enzyme if a reaction is used in which a second substrate is a vaporous substance. In this case, the second substrate and either the first substrate or enzyme is present in a known amount, so that with the presence of either the enzyme or the first substrate a decrease in the mass spectrometer count rate of the second, vaporous substrate occurs.

Except in this last case in which a vaporous substrate is used to measure either a non-vaporous substrate or enzyme, it is preferred to conduct the process of this invention in a manner such that any traces of the expected vaporous product are removed from the system prior to conducting the reaction with the substrate. Thus, it is preferred that the vapor detecting means be employed in a vacuum in the absence of the desired vaporous product. By operating in this manner, any measurement of vapor product other than that produced as a result of the reaction of the substrate is substantially or completely eliminated. Of course, it is possible to conduct the process of this invention without employing a vacuum. When operating in this manner, it is necessary to calibrate the instrument in order to measure the background concentration of the vaporous product.

In use, the apparatus is calibrated by measuring the concentration of a vaporous product of the reaction of a known concentration of the molecule being tested. In this manner, a curve is established which relates the vapor concentration measured with the concentration of the molecule being tested. Generally, these curves show a linear relationship between vapor measurements and concentration for enzyme, and an initially linear relationship which gradually levels off at an asymptote for substrate. Once the response curve for the apparatus is established, the apparatus can be employed to measure the concentration of a molecule by reading the vapor concentration measured at any portion of the curve other than the asymptote.

The following examples are intended to illustrate the present invention and are not intended to limit the same.

EXAMPLE I

The response of the apparatus to various concentrations of urease (EC 3.5.1.5) activity were obtained in the following manner using $CO_2$ at mass 44 as the vaporous product. A pump-reservoir, as shown in the figure, provided a steady flow (about $1.5 \times 10^{-1}$ ml-min$^{-1}$) of substrate (0.2 Molar urea) and buffer (sodium phosphate, pH 6.8 with 10 millimolar EDTA) in one tube (stainless steel, 0.020" inner diameter) which joined a second similar tube at a "T" with a steady flow (about $1.5 \times 10^{-1}$ ml-min$^{-1}$) of buffer only. Somewhat upstream from the two entrances to the "T", the first and second tubes each connected to a continuous degasser which removed a significant fraction of the pre-existing $CO_2$ in the liquids flowing through the first and second tubes.

Urease solution (urease from Sigma) in buffer of known activity concentration (u-ml$^{-1}$ or international units of enzyme activity per ml) was loaded into the sample loop (about 1.5 ml) of the sample injection valve. After observation of a baseline count rate at mass peak 44 for $CO_2$, the sample injection valve was used to switch the sample loop into the flow of the second tube. Following a delivery time delay of about four minutes, a transient increase in the mass 44 count rate occurred, then a steady state count rate, and then a return to the baseline count rate. The circular channel adjacent the membrane had a height of about $10^{-2}$ cm and a radius of about 0.6 cm to effect a residence time of the sample within the circular channel of about 2.5 seconds. The steady state count rate values were plotted versus activity concentration, and provided a response curve which was linear (with a sensitivity of $6 \times 10^8$ counts per second per $u^{-1}$-ml) over the range of about $2 \times 10^{-4}$ u-ml$^{-1}$ to $6 \times 10^{-1}$ u-ml$^{-1}$ and the beginning of possible saturation at 6 u-ml$^{-1}$. In this example, the pump and reservoir consisted of constant pressure driven (clean $N_2$ gas) liquid reservoirs, which provided fairly steady flow rates and correspondingly low noise. Blank responses were obtained by following the same sequence but with the substitution of buffer for the enzyme solution in the sample loop. After the response curve is obtained as a calibration, urease activity concentration can be measured in the range $2 \times 10^{-4}$ u-ml$^{-1}$ to 6 u-ml$^{-1}$.

EXAMPLE II

Upon calibrating the apparatus for urease measurement based on direct measurement of the vaporous product $CO_2$ as described in Example I, the apparatus described in Example I was used with approximately the same flow conditions and buffer for a single assay of DOPA decarboxylase (EC 4.1.1.26) from rat brain, also using $CO_2$ as the vaporous product. The substrate tube contained $1.9 \times 10^{-3}$ Molar L-DOPA and $4 \times 10^{-3}$ Molar ascorbic acid in phosphate buffer, pH 6.7. The same loop was loaded with 1.5 ml of supernatent from rat brain and $8 \times 10^{-4}$ Molar pyridoxal 5-phosphate in phosphate buffer, pH 6.7, and allowed to incubate for 15 min. Then, upon switching the sample injection valve, there was a 4 min. time delay consisting of a transit time and mixing at the "T" with the substrate. A transient increase in count rate was observed, then a leveling into steady state and then a return to baseline. Using the calibration of Example I, and following a correction for a three fold dilution of supernatent compared to tissue valves, the observed DOPA decarboxylase activity concentration in rat brain tissue was determined to be $2.3 \times 10^{-2}$ u-m$^{-1}$, which compares favorably with values obtained by other methods (maximum activity concentration of about $3.7 \times 10^{-2}$ u-ml$^{-1}$).

EXAMPLE III

The response of the apparatus to various concentrations of catalase (EC 1.11.1.6) was determined in the following manner, using $O_2$ at mass 32 as the vaporous product. A pump and reservoir, consisting of a 50 ml Glenco syringe (Model No. 19,925-50) driven by a Sage syringe pump (Model No. 355), provided a steady flow of substrate (about 1.5 Molar hydrogen peroxide in sodium phosphate buffer, pH 6.8) in one tube (stainless steel 0.020" inner diameter). The first tube joined a second tube in a "T", with the second similar tube bringing flow from an upstream switching valve, and the third, outflowing similar tube carrying the combined flow to the thin channel next to the membrane, which communicated vaporous molecules to the mass spectrometer. Prior to entering the "T", the liquids passing through the first and second tubes each passed through a continuous degasser, which continuously removed a significant fraction of the pre-existing $O_2$. In this example, the second tube connected to one of two output ports of a switching valve which allowed the steady flow from one of two different syringe pumps to be selected. One syringe pump (the "enzyme" reservoir-pump) contained buffer and catalase of known activity concentration; the second (the "buffer" reservoir-pump) contained only buffer. This arrangement allowed steady state count rates above a baseline to be determined for various known activity concentrations of catalase. Typically, a baseline count rate was observed, using the buffer reservoir-pump, then the switching valve was used to connect to the enzyme reservoir-pump, and a transient increase followed by a steady state count rate was observed. When desired, the switching valve was then used to reconnect to the buffer reservoir-pump, in which case transient decrease in count rate occurred until the baseline was re-established. The steady state count rates above baseline were plotted versus catalase activity concentration, which provided a calibrating response curve over the range $1.5 \times 10^{-2}$ u-ml$^{-1}$ to 5 u-ml$^{-1}$. The response curve was approximately linear over this range, with a sensitivity of about $7 \times 10^8$ counts-per-second-u$^{-1}$-ml. Following determination of the response curve, the apparatus can be used to determine catalase activity concentration in the range $1.5 \times 10^{-2}$ u-ml$^{-1}$ to 5 u-ml$^{-1}$.

EXAMPLE IV

The response of the apparatus to various concentrations of urea was determined by using the enzyme urease (EC 3.5.1.5) and $CO_2$ at mass 44 as the vaporous product. In this example, the two separate reservoirs and pumps for the sample flow and enzyme flow consisted of pressure driven (clean He gas) liquid reservoirs. Urease in phosphate buffer, pH 6.8 with about 10 mM EDTA, at an activity concentration of 12 u-ml$^{-1}$, flow in one tube. A second tube, with a flow of only buffer or, if injected by an upstream sample injection valve, urea plus buffer, joined the first tube in a "tee". In this example, degassing of all solutions (enzyme, buffer and urea+buffer) was accomplished by bubbling clean helium gas through each solution; in addition, a continuous degasser was connected between the enzyme pump-reservoir and the "tee". Known concentrations of urea were placed in the sample loop (here 2.0 ml) of a sample injection valve. After observation of a baseline count rate at mass peak 44 for $CO_2$, the sample injection valve was used to switch the sample loop into the flow of the tube connected to the outlet of the buffer reservoir-pump. Following a delivery time delay of about 2 minutes, a transient increase in the mass 44 count rate occurred, then a steady count rate, and then a return to the baseline count rate. The steady count rate values were plotted versus urea concentration, and provided a response curve over the range of $3 \times 10^{-6}$ M to $1 \times 10^{-2}$ M. Blank responses were obtained following the same sequence, but with buffer only for urea plus buffer. After the response curve is obtained, the apparatus can be used to measure urea concentration in the range $3 \times 10^{-6}$ M to $1 \times 10^{-2}$ M.

I claim:

1. Apparatus for measuring the concentration of a substrate in a fluid which substrate reacts to form a vaporous product when contacted with a fixed amount or concentration of an enzyme or microorganism or for measuring the concentration of an enzyme or microorganism in a fluid which enzyme or microorganism catalyzes a reaction to form a vaporous product when contacted with a fixed amount or concentration of a substrate for the enzyme or microorganism wherein either:

(a) the amount or concentration of the substrate is fixed when measuring enzyme or microorganism concentration, or, (b) the amount or concentration of the enzyme is fixed or the amount or concentration of the microorganism is fixed when measuring the substrate concentration, which comprises means for mixing said substrate and said enzyme or microorganism, means for directing the resulting mixture to a small channel having a height less than about $10^{-1}$ cm. and a length less than about 10 cm., said small channel being positioned adjacent a membrane that is permeable to said vaporous product and means for measuring directly the amount of said vaporous product passing through said membrane.

2. The apparatus of claim 1 having a fixed amount of a first microorganism or a first enzyme to cause the reaction of a substrate with the attendant formation of a first reaction product and a fixed amount of a second microorganism or a second enzyme adapted to effect a second reaction involving said first reaction product to form said vaporous product.

3. The apparatus of claim 2 wherein the means for measuring the amount of vapor passing through the membrane comprises a mass spectrometer.

4. The apparatus of claim 1 adapted to measure the concentration of at least two substrates in a fluid, said apparatus having a fixed amount of at least two materials selected from the group consisting of an enzyme and a microorganism and at least one membrane, wherein each membrane is permeable to a vaporous product of the reaction involving a substrate and one product of said materials.

5. The apparatus of claim 4 wherein the means for measuring the amount of vapor passing through the membrane comprises a mass spectrometer.

6. The apparatus of claim 1 wherein the means for measuring the amount of vapor passing through the membrane comprises a mass spectrometer.

7. The apparatus of claim 1 adapted to measure the concentration of a substrate in a fluid wherein a second vaporous substrate is at the same time also a reactant catalyzed by a fixed amount or concentration of enzyme or microorganism.

* * * * *